(12) United States Patent
Meiere et al.

(10) Patent No.: US 6,809,212 B2
(45) Date of Patent: Oct. 26, 2004

(54) METHOD FOR PRODUCING ORGANOMETALLIC COMPOUNDS

(75) Inventors: Scott Houston Meiere, Williamsville, NY (US); Cynthia A. Hoover, Grand Island, NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 10/459,626

(22) Filed: Jun. 11, 2003

(65) Prior Publication Data

US 2004/0010158 A1 Jan. 15, 2004

Related U.S. Application Data

(60) Provisional application No. 60/388,054, filed on Jun. 12, 2002, and provisional application No. 60/387,998, filed on Jun. 12, 2002.

(51) Int. Cl.[7] .......................... C07F 15/00; C23C 16/00; H01L 21/44
(52) U.S. Cl. ...................... 556/136; 556/137; 438/580; 438/681; 438/686; 427/585; 427/595
(58) Field of Search .................................. 556/136, 137; 438/580, 681, 686; 427/595, 585

(56) References Cited

U.S. PATENT DOCUMENTS

| | | | | |
|---|---|---|---|---|
| 5,783,716 A | | 7/1998 | Baum et al. .................. | 556/136 |
| 5,929,267 A | | 7/1999 | Kadokura ..................... | 556/136 |
| 6,162,712 A | | 12/2000 | Baum et al. .................. | 438/580 |

OTHER PUBLICATIONS

Boardman et al., "[195]Pt NM Study of ($\eta^5$–Cyclopentadienyl)trialkylplatinum(IV) Complexes", *Magnetic Resonance In Chemistry*, vol. 30, 481–489 (1992).
Tagge et al., "Synthesis of a Noval Volatile Platinum Complex for Use in CVD and a Study of the Mechanism of Its Thermal Decomposition in Solution", *J. Am. Chem. Soc.* 1996, 118, 2634–2643.

Seichi Okeya et al., "The Bis($\beta$–Diketonato)Platinum(II) Complexes", *Coordination Compounds*, 65–69.
Kite et al., "Reactions of Trimethyl($\beta$–dioxo)platinum(iv) Complexes with Nitrogen Compounds", *J. Chem. Soc. (A)* 1968.
Henrik Junicke et al., "The First Platinum(IV) Complexes with Glucopyranoside Ligands. A New Coordination Mode of Carbohydrates", *Inorg. Chem.* 1998, 37, 4603–4606.
Hall et al., "Dimethylplatinum (IV) Compounds III*. Acetylacetonate Complexes", *Journal of Organometallic Chemistry*, 67 (1974) 455–466.
Masahiko Hiratani et al., "Platinum Film Growth by Chemical Vapor Deposition Based on Autocatalytic Oxidative Decomposition", *Jornal of The Electrochemical Society*, 148 (8) C524–C527 (2001).
Ju–Hong Kwon et al, "Preparation of Pt thin films deposited by metalorganic chemical vapor deposition for ferroelectric thin films", *Thin Solid Films* 303 (1997) 136–142.
Yea–jer Chen et al., "Low–temperature organometallic chemical vapor deposition of platinum", *Appl. Phys. Lett.*, vol. 53, No. 17, Oct. 24, 1998.

(List continued on next page.)

Primary Examiner—Porfirio Nazario-Gonzalez
(74) Attorney, Agent, or Firm—Gerald L. Coon (57) ABSTRACT

This invention relates to liquid cyclopentadienyltrimethylplatinum compounds selected from (isopropylcyclopentadienyl)trimethylplatinum and (tert-butylcyclopentadienyl) trimethylplatinum. This invention also relates to a process for producing a film, coating or powder by decomposing a cyclopentadienyltrimethylplatinum compound precursor selected from (isopropylcyclopentadienyl)trimethylplatinum and (tert-butylcyclopentadienyl)-trimethylplatinum, thereby producing the film, coating or powder. This invention further relates to a one pot method for producing an organometallic compound comprising reacting a metal source compound, an alkylating agent and a cyclopentadienyl compound under reaction conditions sufficient to produce said organometallic compound.

20 Claims, 1 Drawing Sheet

OTHER PUBLICATIONS

Ziling Xue et al.,"Characterization of (Methylcyclopentadieny)trimethylplatinun and Low–Temperature Organometallic Chemical Vapor Deposition of Platinum Metal", *J. Am. Chem. Soc.* 1989, 111, 8779–8784.

Williams et al., "Studies of Reductive Elimination Reactions to Form Carbon–Oxygen Bonds from Pt(IV.) Complexes", *J. Am. Chem. Soc.* 123, Feb. 23, 2001.

Abel et al., "2,2':6',2"—Terpyridine (terpy) acting as a Fluxional Bidentate Ligand. Part 1. Trimethylplatinum (iv) Halide Complexes (PtXMe$_3$(terpy) †",*J. Chem. Soc. Dalton Trans.* 1993 292–298.

Clark et al., "Reactions of ($\pi$–5–Cyclooctafiene)Organoplatinum(II)Compounds and the Synthesis of Perfluoroalkylplatinum Complexes", *Journal of Organometallic Chemistry*, 59(1973) 411–428.

Jain et al., "The Organic Chamistry of Platinum (IV)", *Advances in Organometallic Chemistry*, vol. 27.

Dryden et al., "Chemical Vapor Deposition of Platinum: New Precursors and Their Properties", *Chem. Mater.*1991, 3, 677–685.

Goswami et al., "Properties of Platinum Films by Liquid–Source MOCVD In H$_2$ and O$_2$", *Integrated Ferrvelectrics*, 2002, vol. 42, pp. 13–23.

Boardman, "($\eta^5$Cyclopentaflenyl)trialkylplatinum Photohydrosilylation Catalysts. Mechanism of Active Catalyst Formation and Preparation of a Novel Bis(silyl)platinum Hydride", *Organometallics 1992*, 11, 4149–4201.

Ziling Xue et al., "Organometallic Chemical Vapor Deposition of Platinum. Reaction Kinetics and Vapor Pressures of Precursors", *Chem. Mater.* 1992, 4, 162–166.

Hill et al., "Electrophilic Platinum Complexes: Methyl Transfer Reactions and Catalytic Reductive Elimination of Ethane from a Tetramethylplatinum (IV) Complex", *Organometallics* 1999, 18, 1408–1418.

Baar et al., "Oxidative Addition to Diplatinum (II) Complexes: Stereoselectivity and Cooperative Effects", *Organometallics* 2000, 19, 2482–2497.

Junicke et al., "Novel Platinum (IV)–Carbohydrate Complexes: Metal Ion Coordination Behavior of Monosaccharides in Organic Solvents", *J. Am. Chem. Soc.* 1999, 121, 6232–6241.

Clegg et al., "IODO(Trimethyl)Platinum (IV)", *Inorganic Syntheses*, 71–74.

Hill et al., "Platinum (II) Complexes of Demethyl Sulfide", *Platinum (II) Complexes of Dimethyl Sulfide*, 149–153.

Katz et al., "The Pentalenylcycloocta–1,5–dienerhodium Anion and Hydropentalenyl Complexes of Thallium, Platinum, and Rhodium", *Journal of the American Chemical Society*, Mar. 1, 1967 1105–1111.

Crane et al., "Mechanistic Studies of CVD Metallization Processes: Reactions of Rhodium and Platinum β–Diketonate Complexes on Copper Surfaces". *J. Am. Chem. Soc.* 2000, 122, 3422–3435.

Path A: Reported two step synthesis. Requires isolation of tetrameric intermediate as well as halide metathesis (shown here with iodide)

Path B: Proposed one pot synthesis. Does not require isolation of tetrameric intermediate or halide metathesis reagent.

Fig. 1

METHOD FOR PRODUCING ORGANOMETALLIC COMPOUNDS

RELATED APPLICATION

This application claims the benefit of U.S. Provisional Application No. 60/388,054, filed Jun. 12, 2002 and U.S. Provisional Application No. 60/387,998, filed Jun. 12, 2002, the disclosures of which are incorporated herein by reference.

FIELD OF THE INVENTION

This invention relates to liquid cyclopentadienyltrimethylplatinum compounds, a process for producing a film, coating or powder therefrom and a one pot method for producing an organometallic compound.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal or metal oxide film on the substrate.

Preferably, chemical vapor deposition precursors are volatile, heat decomposable and capable of producing uniform films under chemical vapor deposition conditions. In producing thin films by chemical vapor deposition processes, precursors that are liquid at room temperature, rather than solids, often are preferred.

Cyclopentadienyltrimethylplatinum compounds are very promising platinum (Pt) chemical vapor deposition precursors. Chemical vapor deposition is a technique for depositing metal films onto a surface. Although chemical vapor deposition precursors are usually preferred in the liquid state, two of the most utilized platinum species, the parent complex (cyclopentadienyl)trimethylplatinum (mp=109° C.) and (methylcyclopentadienyl)trimethylplatinum (mp=30° C.), are both solids (Xue et al. *J. Am. Chem. Soc.* 1989, 111, 8779). Liquid precursors are in most cases easier to deliver and can give more consistent vaporization (i.e., solids may vary in surface area, particle size, and crystallinity which may affect uniform volatility).

The liquid cyclopentadienyltrimethylplatinum complex (ethylcyclopentadienyl)trimethylplatinum has been disclosed in U.S. Pat. No. 5,929,267, where it was utilized to form platinum films. The compound was characterized by $^1$H NMR and CH analysis. Estimates of melting point (<−78° C.), density (~1.5 g/cm$^3$), and viscosity (~5 cP) are included. Trace metals analysis indicates impurities in the low ppm range. TG-DTA indicates approximately 0% non-volatile residue. The vapor pressure was found to be 0.3 torr at 50–55° C. The compound is reported to be stable to air and water, as well as to temperatures up to 150° C. (although no half-life data was presented). The yield for this precursor, however, is moderate at 51% from iodotrimethylplatinum.

Also, synthesizing organometallic platinum compounds on a large scale basis has not been disclosed. Cyclopentadienyltrimethylplatinum complexes have been synthesized from Pt(IV) (e.g., $K_2PtCl_6$) and Pt(II) (e.g., $K_2PtCl_4$) sources. However, both routes proceed through a Pt(IV) trimethyl species of the general formula $[XPt(CH_3)_3]_4$ (X=halide (e.g., I))(see FIG. 1, Path A). This tetramer can be made increasingly reactive by adding a halide metathesis reagent such as a silver salt (e.g., silver triflate). Isolation of the tetrameric species is commonly achieved via extraction, precipitation, trituration, and filtration. This tetrameric compound can then be used for the formation of a number of other trimethylplatinum containing compounds, including the cyclopentadienyl moieties. No attempt to synthesize a cyclopentadienyltrimethylplatinum complex by a direct route from $K_2PtCl_6$ or $K_2PtCl_4$, without isolation of an intermediate as discussed above, has been disclosed.

In developing methods for forming thin films by chemical vapor deposition methods, a need continues to exist for chemical vapor deposition precursors that preferably are liquid at room temperature, have relatively high vapor pressure and can form uniform films. Therefore, a need continues to exist for developing new compounds and for exploring their potential as chemical vapor deposition precursors for film depositions. It would therefore be desirable in the art to provide a chemical vapor deposition precursor in liquid form and producable with high yields, for example, a liquid cyclopentadienyltrimethylplatinum precursor.

Also, it would be a significant advancement in the art to provide a method capable for a scale up production of organometallic platinum compounds with significant platinum recovery. Further, it would be a significant advancement in the art to synthesize a organometallic platinum compounds using a one step process where all manipulations are carried out in a single vessel, and which route to this family of compounds does not require the isolation of an intermediate complex.

SUMMARY OF THE INVENTION

This invention relates in part to liquid cyclopentadienyltrimethylplatinum compounds selected from (isopropylcyclopentadienyl)trimethylplatinum and (tert-butylcyclopentadienyl)trimethylplatinum. This invention also relates in part to a process for producing a film, coating or powder by decomposing a cyclopentadienyltrimethylplatinum compound precursor selected from (isopropylcyclopentadienyl)trimethylplatinum and (tert-butylcyclopentadienyl)-trimethylplatinum, thereby producing the film, coating or powder. This invention further relates in part to a one pot method for producing an organometallic compound comprising reacting a metal source compound, an alkylating agent and a hydrocarbon or heteroatom-containing compound, e.g., cyclopentadienyl compound, under reaction conditions sufficient to produce said organometallic compound.

The invention has several advantages. For example, the method of the invention is useful in generating organometallic compound precursors that have varied chemical structures and physical properties. The method can be employed to produce organometallic compounds, such as, for instance, cyclopentadienyltrimethylplatinum compounds. The method of the invention is capable for a scale up production of organometallic platinum compounds with significant platinum recovery. The method is particularly well-suited for scale-up production since it can be conducted using the same equipment, some of the same reagents and process parameters that can easily be adapted to manufacture a wide range of products. The method provides for the synthesis of organometallic compounds using a one step process where all manipulations are carried out in a single vessel, and which route to this family of compounds does not require the isolation of an intermediate complex.

DETAILED DESCRIPTION OF THE INVENTION

As indicated above, this invention relates in part to a process for producing a film, coating or powder. The process includes the step of decomposing at least one cyclopentadienyltrimethylplatinum compound precursor selected from (isopropylcyclopentadienyl)trimethylplatinum and (tert-butylcyclopentadienyl)-trimethylplatinum, thereby producing the film, coating or powder, as further described below.

This invention also relates in part to a 'one-pot' procedure for producing organometallic compounds that facilitates both scale up and platinum recovery. With no loss in yield compared to prior art methods, this invention avoided labor-intensive and waste generating material manipulations such as extractions. This method of this invention also eliminates the formation and isolation of a common intermediate, as well as reduced the amount of materials (e.g., chemical reagents, glassware) required substantially, including corrosive HCl. Furthermore, because all transformations occur in one vessel until the final product is isolated (via sublimation/distillation), all other platinum compounds (e.g., side-products) are confined to one location. Since platinum is an expensive metal, recycling the reaction residue to recover the remaining platinum is an economic advantage, and a 'one-pot' methodology is more conducive to this procedure. The product yield can range from about 60 to 99% or greater, preferably from about 75 to 99% or greater, and more preferably from about 80 to 99% or greater.

The method of this invention offers unexpected advantages in a number of ways. The yield for this material is 85–90% from $K_2PtCl_6$ using a simplified one-pot synthetic scheme which facilitates both scale up and platinum recovery. The compound is a liquid, unlike (cyclopentadienyl)trimethylplatinum and (methylcyclopentadienyl)trimethylplatinum. Taking into account that iodotrimethylplatinum is synthesized from $K_2PtCl_6$ in ~85% yield, the direct comparison to the ethylcyclopentadienyl preparation cited above would be adjusted to 85–90% versus 43%. For an expensive material such as platinum, this twofold increase is a significant advantage. Furthermore, ethylcyclopentadiene is available as a dimer commercially at 97% purity, thus requiring cracking and fractional distillation to remove unsubstituted cyclopentadiene followed by a deprotonation methodology. The analogous isopropyl substituted ligand is available as a sodium salt in >99% purity.

(Isopropylcyclopentadienyl)trimethylplatinum is a yellow liquid (mp=−38° C., bp=122° C. at 5 torr, d=1.43 g/mL at 24° C., viscosity=2.7 cP at 30° C.). The half-life (i.e., thermal stability) of the compound is approximately 0.5 hr at 150° C. The compound does slowly darken in color if left exposed to air, so storage under nitrogen is required. Purity was measured by GC-MS (>99.5%), $^1H$ NMR (>99%), TGA (>99.5%), and ICP-MS (>99.9%).

This invention further relates in part to liquid platinum precursors selected from (isopropylcyclopentadienyl)trimethylplatinum and (tert-butylcyclopentadienyl)trimethylplatinum. This liquid platinum precursors may exhibit performance and cost advantages over currently available precursors. The liquid platinum precursors can be prepared by conventional methods known in the art or by the one pot method of this invention. Preferably, the liquid platinum precursors of this invention are prepared by the one pot method of this invention that involves reacting a platinum source compound, an alkylating agent and a cyclopentadienyl compound under reaction conditions sufficient to produce said liquid platinum precursor compound.

As indicated herein, this invention involves a one pot method for producing an organometallic compound comprising reacting a metal source compound, an alkylating agent and a hydrocarbon or heteroatom-containing compound, e.g., cyclopentadienyl or cyclopentadienyl-like compound, under reaction conditions sufficient to produce said organometallic compound. The method of the invention is capable for a scale up production of organometallic platinum compounds with significant platinum recovery. The method is particularly well-suited for scale-up production since it can be conducted using the same equipment, some of the same reagents and process parameters that can easily be adapted to manufacture a wide range of products. The method provides for the synthesis of organometallic compounds using a one step process where all manipulations are carried out in a single vessel, and which route to this family of compounds does not require the isolation of an intermediate complex.

The metal source compound may be selected from a wide variety of metal-containing compounds known in the art. Illustrative metals include platinum, palladium and nickel, preferably platinum. The metal source compound is preferably any platinum metal compound, more preferably $M_2PtX_6$ (where M is alkali metal, alkaline earth metal, silver, or ammonium, and X is halide); and most preferably $K_2PtCl_6$.

The concentration of the metal source compound can vary over a wide range, and need only be that minimum amount necessary to provide the given metal concentration desired to be employed and which will furnish the basis for at least the amount of metal necessary for the organometallic compounds of this invention. In general, depending on the size of the reaction mixture, metal source compound concentrations in the range of from about 1 millimole or less to about 1000 millimoles or greater, should be sufficient for most processes.

The alkylating agent may be selected from a wide variety of metal-containing compounds known in the art. Illustrative alkylating agents include $R_2CuLi$ (where R is alkyl); RMgX (where R is alkyl, X is halide); and RLi (where R is $CH_3$ for trimethylplatinum synthesis).

The concentration of the alkylating agent can vary over a wide range, and need only be that minimum amount necessary to provide the given alkyl concentration desired to be employed and which will furnish the basis for at least the amount of alkyl groups necessary for the organometallic compounds of this invention. In general, depending on the size of the reaction mixture, alkylating agent concentrations in the range of from about 1 millimole or less to about 1000 millimoles or greater, should be sufficient for most processes.

The solvent employed in the method of this invention may be any saturated and unsaturated hydrocarbons, aromatic hydrocarbons, aromatic heterocycles, alkyl halides, silylated hydrocarbons, ethers, polyethers, thiosthers, esters, lactones, amides, amines, polyamines, nitrites, silicone oils, other aprotic solvents, or mixtures of one or more of the above;

more preferably hexanes, pentanes, or dimethoxyethanes; and most preferably diethylether or THF. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting material.

Reaction conditions such as temperature, pressure and contact time may also vary greatly and any suitable combination of such conditions may be employed herein. The reaction temperature may be the reflux temperature of any of the aforementioned solvents, and more preferably between about −100° C. to about 65° C., and most preferably between about 0° C. to about 25° C. Normally the reaction is carried out under ambient pressure and the contact time may vary from a matter of seconds or minutes to a few hours or greater. The reactants can be added to the reaction mixture or combined in any order.

The quencher may be selected from a wide variety of compounds known in the art. Illustrative quenchers used in this invention include alkyl halides, ketones, alcohols, water, mineral acids, organic acids, carboxylic acids; and more preferably 1-bromo-2-chloroethane, 1-bromo-2-fluoroethane, iodomethane; and most preferably 1,2-dibromoethane.

The concentration of the quencher can vary over a wide range, and need only be that minimum amount necessary to prepare the organometallic compounds of this invention. In general, depending on the size of the reaction mixture, quencher concentrations in the range of from about 1 millimole or less to about 1000 millimoles or greater, should be sufficient for most processes.

The organometallic compounds prepared by the methods of this invention can be represented by the formula $LM(R)_3$, preferably $LPt(R)_3$, where L is a hydrocarbon or hereroatom-containing group that may be selected from carbohydrates, tris(pyrazolyl)borates, 3 pyridines, bipyridines, tripyridines, 3 phosphines, diphosphines, triphosphines, 3 amines, diamines, triamines; more preferably β-diketonates, R is a linear or branched alkane or silane group, and M is a metal selected from platinum, palladium and nickel. Preferably, L is selected from pentahapto, un-, mono-, di-, tri-, tetra-, pentasubstituted cyclopentadienyl, indenyl, cyclic and acyclic allyls; R is methyl, and M is platinum. More preferably, L is selected from cyclopentadienyl and cyclopentadienyl-like compounds. Examples of cyclopentadienyl-like moieties include cyclo-olefin e.g., cyclohexadienyl, cycloheptadienyl, cyclooctadienyl rings, heterocyclic rings, aromatic rings, such as substituted or unsubstituted benzenyl, and others, as known in the art.

The concentration of the hydrocarbon or heteroatom-containing compound providing L can vary over a wide range, and need only be that minimum amount necessary to provide the given L concentration desired to be employed and which will furnish the basis for at least the amount of L groups necessary for the organometallic compounds of this invention. In general, depending on the size of the reaction mixture, L compound concentrations in the range of from about 1 millimole or less to about 1000 millimoles or greater, should be sufficient for most processes.

When a cyclopentadienyl compound is employed in the reaction, the cyclopentadienyl (or substituted analog) delivery may occur by a non-deprotonated diene (e.g., cyclopentadiene), preferably a lithium, potassium, thallium, ammonium, calcium, or magnesium salt of the cyclopentadientl compound. The addition may be as a solid or in the alternative, as a solution with any solvents listed above, preferably the sodium salt in ~1–2M solution.

The stir time employed in the method of this invention can range from about 0.1 to about 200 hours for all steps, more preferably from about 2 to about 100 hours for alkylation, e.g., methylation, from about 2 to about 72 hours for quenching, and from about 0.1 to about 48 hours for cyclopentadienyl addition. More preferably, the stir time can range from about 2 to 16 hours for methylation, 2 to 16 hours for quenching, and 0.1 to 1 hour for cyclopentadienyl addition.

For organometallic compounds prepared by the method of this invention, purification can occur through recrystallization, more preferably through extraction of reaction residue (e.g., hexane) and chromatography, and most preferably through sublimation and distillation.

Those skilled in the art will recognize that numerous changes may be made to the method described in detail herein, without departing in scope or spirit from the present invention as more particularly defined in the claims below.

Examples of techniques that can be employed to characterize the cyclopentadienyltrimethylplatinum compounds formed by the synthetic methods described above include, but are not limited to, analytical gas chromatography, nuclear magnetic resonance, thermogravimetric analysis, inductively coupled plasma mass spectrometry, vapor pressure and viscosity measurements.

Relative vapor pressures, or relative volatility, of cyclopentadienyltrimethylplatinum compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

Cyclopentadienyltrimethylplatinum compound precursors described herein are liquid at room temperature and are well suited for preparing in-situ powders and coatings. For instance, a liquid cyclopentadienyltrimethylplatinum compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying a cyclopentadienyltrimethylplatinum compound precursor, and heating and decomposing it, thereby forming a first layer, followed by at least one other coating with the same or a different precursors, and heating.

Liquid cyclopentadienyltrimethylplatinum compound precursors such as described above also can be atomized and sprayed onto a substrate. Atomization and spraying means, such as nozzles, nebulizers and others, that can be employed are known in the art.

In preferred embodiments of the invention, a cyclopentadienyltrimethylplatinum compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one cyclopentadienyltrimethylplatinum compound precursor, such as described above, also can be employed in a given process.

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the cyclopentadienyltrimethylplatinum compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2$), water vapor, organic vapors and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

Deposition processes described herein can be conducted to form a film, powder or coating that includes a single metal, e.g, a Pt-film, or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the cyclopentadienyltrimethylplatinum compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of platinum, for instance, can be considered for fabricating metal electrodes, in particular as p-channel metal electrodes in logic, and as capacitor electrodes for DRAM applications.

The process also is suited for preparing layered films, wherein at least two of the layers differ in phase or composition. Examples of layered film include metal-insulator-semiconductor, and metal-insulator-metal.

In an embodiment, the invention is directed to a process that includes the step of decomposing vapor of a cyclopentadienyltrimethylplatinum compound precursor described above, thermally, chemically, photochemically or by plasma activation, thereby forming a film on a substrate. For instance, vapor generated by the compound, a liquid at room temperature, is contacted with a substrate having a temperature sufficient to cause the cyclopentadienyltrimethylplatinum compound to decompose and form a film on the substrate.

The cyclopentadienyltrimethylplatinum compound precursors can be employed in chemical vapor deposition or, more specifically, in metalorganic chemical vapor deposition processes known in the art. For instance, the cyclopentadienyltrimethylplatinum compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The cyclopentadienyltrimethylplatinum compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The process of the invention can be conducted in various chemical vapor deposition reactors, such as, for instance, hot or cold-wall reactors, plasma-assisted, beam-assisted or laser-assisted reactors, as known in the art.

Precursors that are liquid at room temperature are preferred during chemical vapor deposition manufacturing and (isopropylcyclopentadienyl)trimethylplatinum and (tert-butylcyclopentadienyl)trimethylplatinum. have properties that make them suitable as chemical vapor deposition precursors.

Examples of substrates that can be coated employing the process of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The process of the invention can be conducted to deposit a film on substrate that has a smooth, flat surface. In an embodiment, the process is conducted to deposit a film on a substrate used in wafer manufacturing or processing. For instance, the process can be conducted to deposit a film on patterned substrates that include features such as trenches, holes or vias. Furthermore, the process of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometer thick. Films that are less than 50 nanometer thick, for instance, films that have a thickness between about 20 and about 30 nanometer, also can be produced.

Cyclopentadienyltrimethylplatinum compound precursors described above also can be employed in the process of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. millimeters) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The process of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more cyclopentadienyltrimethylplatinum compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the cyclopentadienyltrimethylplatinum compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above a cyclopentadienyltrimethylplatinum compound precursor can be used alone or in combination with one or more components, such as, for example, other organometallic precursors, inert carrier gases or reactive gases.

In a system that can be used in producing films by the process of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The cyclopentadienyltrimethylplatinum compound precursors described above can be employed to produce films that include a single metal, e.g, a Pt-film, or a film that includes a single metal oxide. Mixed films also can be deposited, for instance mixed metal oxide films. Such films are produced, for example, by employing several organometallic precursors, at least one of which being selected from the cyclopentadienyltrimethylplatinum compounds described above. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

EXAMPLE 1

Figure 1:
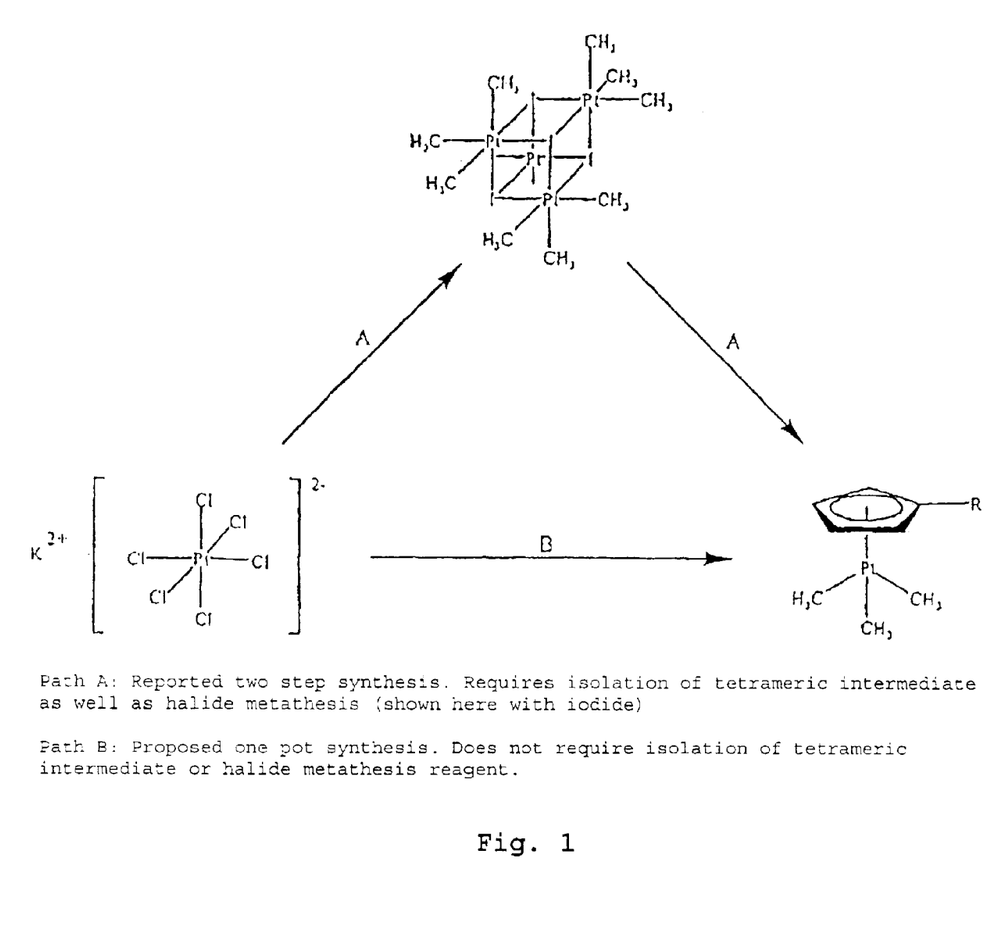
FIG. 1 depicts a new synthetic route for preparing cyclopentadienyltrimethylplatinum compounds (B) and a prior art synthetic route used to prepare cyclopentadienyltrimethylplatinum compounds (A).

The reaction depicted in FIG. 1, Path A was performed as reported by Boardman and Newmark (*Magnetic Resonance in Chemistry* 1992, 30, 481) for the synthesis of other cyclopentadienyl platinum complexes. In the present case, utilizing sodium isopropylcyclopentadienide yielded a new compound not previously synthesized. The yield for the synthesis of iodotrimethylplatinum was 80% (reported as 89%). The subsequent yield for (isopropylcyclopentadienyl) trimethylplatinum (a yellow liquid) was 88%. Overall yield (two-steps) was 70%.

EXAMPLE 2

The reaction depicted in FIG. 1, Path B was performed. All glassware was oven-dried overnight. A 2 L three-neck round-bottom flask, charged with a stir bar, was fitted with a septum-capped addition funnel, a vacuum adaptor connected to a Schlenk line, and a septum. After drying under nitrogen, the flask septum was removed briefly to add $K_2PtCl_6$ (41.5 g, 85.5 mmol). The system was re-purged once more with nitrogen. Anhydrous, inhibitor-free tetrahydrofuran (THF) (850 mL) was pressure transferred into the addition funnel and added to the flask. Stirring was commenced and the yellow slurry was cooled to 0° C. A diethylether solution of 1.4M methyllithium (500 mL, 700 mmol) was pressure transferred into the addition funnel. The methyllithium solution was added dropwise (over 5–6 hr) at a rate such that the temperature of the reaction mixture was held below 5° C. at all times. A slower rate of addition was necessary at the beginning of the addition, with only 20% of the total volume added after 2 hr. Once the methyllithium addition was completed, the reaction mixture was allowed to warm to room temperature. The yellow-brown suspension faded to light tan as stirring continued overnight (~16 hr). The suspension was cooled once more to 0° C. Nitrogen-purged 1,2-dibromoethane (40 mL, 460 mmol) was added dropwise (over 2–3 hr) at a rate such that the temperature of the reaction mixture was held below 5° C. at all times. A slower rate of addition was necessary at the beginning of the addition, with only 20% of the total volume added after almost 2 hr. The reaction mixture was allowed to stir at 0° C. for ~4 hr, then allowed to warm to room temperature while stirring overnight (~16 hr). The solvent and excess 1,2-dibromoethane were removed under reduced pressure (~0.1 torr) and gentle heat (30–40° C.). The solid was left under vacuum for 3 hr. The brown residue was suspended in THF and sodium isopropylcyclopentadienide (12.2 g, 94 mmol) was added as a 0.6 M THF solution (over 20–30 minutes) by pressure transfer. After stirring 1 hr, the solvent was removed under reduced pressure, and the product was isolated via 'short path' distillation to yield a yellow liquid in 87% yield.

EXAMPLE 3

The reaction depicted in FIG. 1, Path B was performed. All glassware was oven-dried overnight. A three-neck round-bottom flask, charged with a stir bar, was fitted with a septum-capped addition funnel, a vacuum adaptor connected to a Schlenk line, and a septum. After drying under nitrogen, the flask septum was removed briefly to add $K_2PtCl_6$ (4.15 g, 8.55 mmol). The system was re-purged once more with nitrogen. Anhydrous, inhibitor-free tetrahydrofuran (THF) (85 mL) was pressure transferred into the addition funnel and added to the flask. Stirring was commenced and the yellow slurry was cooled to 0° C. A diethylether solution of 1.4M methyllithium (50 mL, 70 mmol) was pressure transferred into the addition funnel. The methyllithium solution was added dropwise (over 3–4 hr) at a rate such that the temperature of the reaction mixture was held below 5° C. at all times. A slower rate of addition was necessary at the beginning of the addition, with only 20% of the total volume added after 1 hr. Once the methyllithium addition was completed, the reaction mixture was allowed to warm to room temperature. The yellow suspension faded to colorless after 3–4 hr as stirring continued. The reaction was left to stir overnight (~16 hr). The suspension was cooled once more to 0° C. Nitrogen-purged 1,2-dibromoethane (4.0 mL, 46 mmol) was added dropwise (over 1 hr) at a rate such that the temperature of the reaction mixture was held below 5° C. at all times. A slower rate of addition was necessary at the beginning of the addition, with only 20% of the total volume added after almost 1 hr. The reaction mixture was allowed to stir at 0° C. for ~4 hr, then allowed to warm to room temperature while stirring overnight (~16 hr). The solvent and excess 1,2-dibromoethane were removed under reduced pressure (~0.1 torr) and gentle heat (~30° C.). To facilitate complete removal of 1,2-dibromoethane, a small amount of THF was added to the solid residue and re-evaporated. The solid was left under vacuum for 3 hr. The brown residue was suspended in THF and sodium methyl-cyclopentadienide (prepared from doubly distilled methyl-cyclopentadiene and NaH) (1.0 g, 10 mmol) was added as a 1.3M THF solution (over 15 minutes) by pressure transfer. After stirring 1 hr, the solvent was removed under reduced pressure (~0.5 torr). The product was isolated via 'short path' distillation or sublimation (reported sublimation temperature: 23° C. at 0.053 mm) to yield white crystals in 65–75% yield. Purity: >99.5% by GC/MS, >99% by NMR, <0.1% NVR by TGA.

EXAMPLE 4

Preparation of (Methylcyclopentadienyl)trimethylplatinum Using Methyllithium and 20 Volumes of THF in the Alkylation Step An oven-dried 500 mL, four-neck, round-bottom flask equipped with a magnetic stirring bar, a thermocouple, two pressure-equalizing addition funnels, and a nitrogen/vacuum line connected to a gas bubbler was charged with potassium hexachloroplatinate (10 g, 20.58 mmol). The system was sealed and briefly evacuated, then purged with nitrogen. The purge cycle was repeated twice. Anhydrous, inhibitor-free THF (200 mL, 20 vol) was pressure-transferred into an addition funnel using a slightly positive nitrogen pressure (3–5 psi), then drained into the flask. The resulting yellow slurry was cooled to 0° C. using an ice/ethanol bath then purged twice with nitrogen. A solution of methyllithium in diethyl ether (105.5 mL, 1.6 M, 168.8 mmol, 8.2 equiv) was pressure transferred into an addition funnel using a slightly positive nitrogen pressure (3–5 psi), then added in 2–5 mL portions and 15 min intervals over 6.5 h while maintaining the temperature of the reaction mixture between −2 and 4° C. The initially bright yellow slurry turned yellow/tan within 1 h. Upon each subsequent addition of methyllithium, the tan hue faded briefly but was regenerated as the reaction progressed. At the end of methyllithium addition, the batch appearance was a light yellow/tan and turbid solution. The reaction mixture was allowed to slowly warm to ambient temperature overnight. After further stirring for 14 h, the batch appearance was an off-white, turbid solution. The reaction mixture was cooled to 0° C. and the reaction quenched by slowly adding nitrogen-purged 1,2-dibromoethane (10 mL, 5.2 equiv) via an addition funnel over 3 h. A copious gas evolution was observed at the beginning of the quench, but this evolution subsided after approximately 4 mL of dibromoethane had been added. The reaction mixture was allowed to warm to ambient temperature and further stirred for 18 h to afford a tan, turbid solution. The flask was set in a heating mantle, fitted with a short path distillation head, and the bulk of solvents distilled at 35° C. under moderate vacuum (approximately 140 mmHg). Residual 1,2-dibromoethane was further removed at 1.5 torr and 35–40° C. for 3 h. Anhydrous, inhibitor-free THF (80 mL, 8 vol) was added to the flask and the resulting suspension vigorously stirred to afford a brown suspension of fine solids. A solution of MeCpLi in THF/hexanes [60 mL, 0.38 M, 1.1 equiv] was slowly added to the suspension over 30 min and the resulting mixture stirred at ambient temperature for 1 h. The brown slurry was pressure-transferred into a dry, 500-mL, round-bottom flask and the solvent stripped on a rotary evaporator under reduced pressure at 28 C to give a brown, mobile slurry. Anhydrous heptane (200 mL, 20 vol) was added to the slurry and the suspension was vigorously stirred. A large quantity of solids adhered to the flask as a result of heptane addition. Stirring was discontinued and the solids allowed to settle. The supernatant was pressure-transferred into a 500-mL flask and concentrated on a rotary evaporator at 28–35° C. to afford a yellow-brown, oily residue [7.95 g]. The product was purified by vacuum distillation (0.13 torr, bp 46–47 C) to afford the title complex in 68.5% yield [4.5 g]. Analysis by GC indicated a purity of 92.5% (AUC) with 0.9% (AUC) (methylcyclopentadienyl)trimethylplatinum and 5.8% (AUC) dodecane contaminant carried from n-hexyllithium used to prepare MeCpLi from MeCp monomer. The $^1$H NMR spectrum was consistent with the assigned structure.

EXAMPLE 5

Preparation of (Methylcyclopentadienyl)trimethylplatinum Using Methyllithium and 10 Volumes of THF in the Alkylation Step A dry 500 mL, three-neck, round-bottom jacketed flask equipped with a magnetic stirring bar, a thermocouple, a pressure-equalizing addition funnel, and a nitrogen/vacuum line connected to a gas bubbler was charged with potassium hexachloroplatinate (10 g, 20–58 mmol). The system was sealed and briefly evacuated, then purged with nitrogen. The purge cycle was repeated twice. Anhydrous, inhibitor-free THF (100 mL, 10 vol) was pressure-transferred into the addition funnel using a slightly positive nitrogen pressure (3–5 psi), then drained into the flask. The resulting yellow slurry was cooled to 0° C. using a chiller then purged twice with nitrogen. A solution of methyllithium in diethyl ether (105.5 mL, 1.6 M, 168.8 mmol, 8.2 equiv) was pressure-transferred into the addition funnel using a slightly positive nitrogen pressure (3–5 psi), then added in 2–5 mL portions over 6 h while maintaining the temperature of the reaction mixture between 0–2° C. The chiller was turned off and the reaction mixture allowed to slowly warm to ambient temperature and stir overnight. The reaction mixture was cooled to 0 C and the reaction quenched by slowly adding nitrogen-purged 1,2-dibromoethane (10 mL, 5.2 equiv) via an addition funnel over 2 h. The reaction mixture was allowed to warm to ambient temperature and further stir overnight to afford a tan, turbid solution. The flask was fitted with a short-path distillation head, the chiller fluid was set to 40° C., and the bulk of solvents distilled at 35° C. under moderate vacuum (approximately 140 mmHg). Residual 1,2-dibromoethane was further removed at 1.0 torr and 40° C. for 2 h. Anhydrous, inhibitor-free TBF (100 mL, 10 vol) was added to the brown solid residue and the resulting suspension vigorously stirred to afford a brown suspension of fine solids. Analysis of an aliquot from the slurry by GC indicated that a small amount of dibromoethane was still present in the residue. The solvent was further distilled as described above, the residue suspended in THF (80 mL, 8 vol) and stirred to afford a brown slurry. Further GC analysis indicated that only a trace amount of dibromoethane was present in the residue. A solution of MeCpLi in THF/hexanes [63 mL, 0.36 M, 1.1 equiv] was slowly added to the suspension over 30 min and the resulting mixture stirred at ambient temperature for 1 h. The bulk of THF was distilled under reduced pressure (140 mmHg, 35° C., removing approximately 60 mL THF). To the resulting brown slurry was added anhydrous heptane (200 mL, 20 vol), and the suspension was vigorously stirred for 1 h to extract the product. Stirring was discontinued, the solids allowed to settle, and the supernatant was pressure-transferred into a 500-ml flask. To the solid residue were added anhydrous THF (40 mL) and anhydrous heptane (160 mL), and the suspension was vigorously stirred for 1 h to further extract the product. The supernatant was combined with the initial extracts and the solvents removed under reduced pressure on a rotary evaporator to afford a yellow-brown slurry. Anhydrous THF (50 mL) was added to the slurry, the resulting brown solution transferred to a 100-mL flask and the solvents further removed under reduced pressure to afford a brown oil [12.59 g]. The product was purified by vacuum distillation (0.3 to 0.4 torr, bp 56–57° C.] to afford the title complex in 61% yield [4.01 g]. The initially isolated colorless oil solidified on standing at ambient temperature to afford an off-white solid (mp=29–30° C. Analysis by GC indicated a purity of >99% (AUC) with <0.1% (AUQ) (methylcyclopentadienyl) trimethylplatinum. The $^1$H NMR spectrum was consistent with the assigned structure. Further trace metal analysis by ICPMS indicated 3.57 ppm for all combined trace metals, hence >99.999% Pt content.

EXAMPLE 6
Preparation of (Methylcyclopentadienyl)trimethylplatinum Using Methylmagnesium Chloride in the Alkylation Step A dry, 500 mL, three-neck, round-bottom flask equipped with a magnetic stirring bar, a thermocouple, a pressure-equalizing addition funnel, and a nitrogen/vacuum line connected to a gas bubbler was charged with potassium hexachloroplatinate (10 g, 20.5 8 mmol). The system was sealed and briefly evacuated, then purged with nitrogen. The purge cycle was repeated twice. Anhydrous, inhibitor-free THF (100 mL, 10 vol) was pressure-transferred into the addition funnel using a slightly positive nitrogen pressure (3–5 psi), then drained into the flask. The resulting yellow slurry was cooled to 0° C. using an ice/ethanol bath then purged twice with nitrogen. A solution of methylmagnesium chloride in TBF (56.3 mL, 3.0 M, 168.8 mmol, 8.2 equiv) was pressure-transferred into the addition funnel using a slightly positive nitrogen pressure (3–5 psi), then added dropwise to the slurry over 1 h. The reaction mixture was allowed to slowly warm to ambient temperature and stir overnight. The reaction mixture was cooled to 0° C. and the reaction quenched by slowly adding nitrogen-purged 1,2-dibromoethane (10 mL, 5.2 equiv) in a single portion. The reaction mixture was allowed to warm to ambient temperature and further stir for 2.5 d. The flask was fitted with a short path distillation head and a heating mantle and the bulk of solvents were distilled at 35° C. under moderate vacuum (approximately 140 mmHg). Residual 1,2-dibromoethane was further removed at 1.0 torr and 40° C. for 2 h. Anhydrous, inhibitor-free THF (80 mL, 8 vol) was added to the off-white solid residue and the suspension was vigorously stirred for 4 h at ambient temperature. A solution of MeCpLi in THF/hexanes [60 mL, 0.38 M, 1.1 equiv] was slowly added to the slurry over 30 min and the resulting mixture vigorously stirred at ambient temperature for 4 h. The resulting slurry was transferred to a 500 mL flask and THF was removed on a rotary evaporator to afford a yellow-brown solid residue. Anhydrous heptane (200 mL) was added to the residue but solubilization could not be achieved. Anhydrous TBF (200 mL) was added, the flask fitted with a Claisen adapter and a mechanical stirrer, and the suspension was stirred at ambient temperature overnight. The supernatant was transferred to a 500 mL flask then stripped on a rotary evaporator using a 100 mL flask to afford a yellow-brown, oily residue [12.87 g]. Purification by distillation at 0.25 to 0.50 torr (bp 55° C.) afforded (methylcyclopentadienyl)trimethylplatinum in 41% yield [2.7 g].

EXAMPLE 7
Preparation of Lithium Methylcyclopentadienide

A 500 mL, two-neck, round-bottom flask equipped with a magnetic stirring bar, a thermocouple, and a 12 cm jacketed Vigreux column equipped with a short path condenser was charged with methyl cyclopentadiene dimer (200 mL). The condenser was fitted with a nitrogen inlet adapter and a receiving flask cooled to −70 to −75° C. using an acetone/CO$_2$ bath. The flask contents were brought to a gentle reflux (145–170° C.) and the initial approximately 70 mL of distillate was collected and discarded. The distillation was carried out under a slightly positive nitrogen atmosphere to minimize condensation of ambient moisture into the distillate. The bulk of methyl cyclopentadiene dimer (approximately 125 mL) was collected at 50–53° C. The distillation was repeated twice, again discarding approximately 25–30% of the forerun to afford 26 g of methyl cyclopentadiene monomer [324.5 mmol, 96.2% AUC, with 0.7% residual cyclopentadiene monomer]. To the cold, freshly cracked methyl cyclopentadiene was added anhydrous, inhibitor-free THF (300 mL) and the resulting solution was briefly evacuated and purged with nitrogen three times. A solution of n-butyllithium in hexanes (2.5 M, 118 mL, 0.9 equiv) was added dropwise via a pressure-equalizing addition funnel over 30 min while efficiently stirring the reaction mixture and cooling the flask with an acetone/CO$_2$ bath. The cooling bath was removed and the reaction mixture allowed to warm to ambient temperature overnight. The initially light yellow solution became a yellow slurry as the reaction progressed. The slurry was pressure-transferred into a dry, three-neck, 1 L, round-bottom equipped with a pressure-equalizing addition funnel and diluted with anhydrous THF until a yellow-orange solution was obtained (this required the addition of 290 mL of THF). Titration of the resulting lithium methylcyclopentadienide solution with diphenylacetic acid indicated that its concentration was 0.38 M.

What is claimed is:

1. A one pot method for producing an organometallic compound comprising reacting a metal source compound, an alkylating agent and a hydrocarbon or heteroatom-containing compound under reaction conditions sufficient to produce said organometallic compound.

2. The one pot method of claim 1 wherein the metal source compound is a platinum metal compound.

3. The one pot method of claim 1 wherein the metal source compound is selected from $M_2PtX_6$ wherein M is an alkali metal, alkaline earth metal, silver, or ammonium, and X is halide.

4. The one pot method of claim 1 wherein the metal source compound is $K_2PtCl_6$.

5. The one pot method of claim 1 wherein the alkylating agent is selected from $R_2CuLi$ wherein R is alkyl; RMgX wherein R is alkyl, and X is halide; and RLi wherein R is $CH_3$.

6. The one pot method of claim 1 which is conducted in the presence of one or more solvents.

7. The one pot method of claim 6 wherein the solvent is selected from saturated and unsaturated hydrocarbons, aromatic hydrocarbons, aromatic heterocycles, alkyl halides, silylated hydrocarbons, ethers, polyethers, thiosthers, esters, lactones, amides, amines, polyamines, nitrites, silicone oils, other aprotic solvents, or mixtures of one or more of the above.

8. The one pot method of claim 1 which is conducted in the presence of a quencher selected from alkyl halides, ketones, alcohols, water, mineral acids, organic acids, carboxylic acids.

9. The one pot method of claim 1 wherein the organometallic compound is represented by the formula $LM(R)_3$ wherein L is a hydrocarbon or hereroatom-containing group selected from carbohydrates, tris(pyrazolyl)borates, 3 pyridines, bipyridines, tripyridines, 3 phosphines, diphosphines, triphosphines, 3 amines, diamines, triamines, R is a linear or branched alkane or silane group, and M is a metal selected from platinum, palladium and nickel.

10. The one pot method of claim 1 wherein the organometallic compound is represented by the formula $LM(R)_3$ wherein L is selected from a cyclopentadienyl or cyclopentadienyl-like compound, R is methyl, and M is platinum.

11. The one pot method of claim 1 wherein the organometallic compound is represented by the formula $LM(R)_3$ wherein L is selected from pentahapto, un-, mono-, di-, tri-, tetra-, pentasubstituted cyclopentadienyl, indenyl, cyclic and acyclic allyls, R is methyl, and M is platinum.

12. The one pot method of claim 1 wherein the organometallic compound yield is from about 75 to 99% or greater.

13. A one pot method for producing a liquid cyclopentadienyltrimethylplatinum compound comprising reacting a platinum source compound, an alkylating agent and a cyclopentadienyl compound under reaction conditions sufficient to produce said liquid cyclopentadienyltrimethylplatinum compound.

14. A liquid cyclopentadienyltrimethylplatinum compound selected from the group consisting of (isopropylcyclopentadienyl)trimethylplatinum and (tert-butylcyclopentadienyl)trimethylplatinum.

15. A process for producing a film, coating or powder by decomposing a liquid cyclopentadienyltrimethylplatinum compound precursor selected from (isopropylcyclopentadienyl)trimethylplatinum and (tert-butylcyclopentadienyl)-trimethylplatinum, thereby producing the film, coating or powder.

16. The process of claim 15 wherein the decomposing of said liquid cyclopentadienyltrimethylplatinum compound precursor is thermal, chemical, photochemical or plasma-activated.

17. The process of claim 15 wherein said liquid cyclopentadienyltrimethylplatinum compound precursor is vaporized and the vapor is directed into a deposition reactor housing a substrate.

18. The process of claim 17 wherein the substrate is comprised of a material selected from the group consisting of a metal; a metal silicide; a semiconductor; an insulator and a barrier material.

19. The process of claim 17 wherein the substrate is a patterned wafer.

20. The process of claim 15 wherein the film, coating or powder is produced by a gas phase deposition.

* * * * *